United States Patent [19]
Pastan et al.

[11] Patent Number: 6,099,842
[45] Date of Patent: Aug. 8, 2000

[54] RECOMBINANT IMMUNOTOXIN COMPOSED OF A SINGLE CHAIN ANTIBODY REACTING WITH THE HUMAN TRANSFERRIN RECEPTOR AND DIPTHERIA TOXIN

[75] Inventors: Ira Pastan, Potomac; Vijay Chaudhary, Rockville; David FitzGerald, Silver Spring; Janendra Batra, Rockville, all of Md.

[73] Assignee: The United States of America as represented by the Department of Health and Human Services, Washington, D.C.

[21] Appl. No.: 07/620,939

[22] Filed: Dec. 3, 1990

[51] Int. Cl.$^7$ .......................... A61K 39/40; A61K 39/42; A61K 39/44; A61K 39/395

[52] U.S. Cl. ...................................... 424/183.1; 424/178.1; 530/391.7

[58] Field of Search ................................ 424/85.8, 183.1, 424/178.1; 530/387, 387.1, 388.22, 350, 391.7

[56] References Cited

U.S. PATENT DOCUMENTS 4,892,827  1/1990  Pastan et al. ............................ 435/193

OTHER PUBLICATIONS

Pastan et al Cell 47 641–648 1986.
Youle et al 1988 Immunotoxins. Frankel A.E. ed. 113–122.
V.K. Chaudhary, et al., A Recombinant Immunotoxin Consisting of Two Antibody Variable Domains Fused to Pseudomonas Exotoxin, Nature, vol. 339, No. 6223, Jun., 1989, pp. 394–397.
J.K. Batra, et al., Single–Chain Immunotoxins Directed at the Human Transferrin Receptor Containing Pseudomonas Exotoxin A or Diphtheria Toxin: Anti–TFR(Fv)–PE40 and DT388–Anti–TFR(Fv), Mol. Cell. Biol., vol. 11, No. 4, Apr., 1991, pp. 220–2205.
V.K. Chaudhary, et al., A Recombinant Single–Chain Immunotoxin Composed of Anti–TAC Variable Regions and A Truncated Diphtheria Toxin, Proc. Natl. Acad. Sci. USA, vol. 87, Dec., 1990, pp. 9491–9494.
J.K. Batra, et al., Anti–TAC(Fv)–PE40: A Single Chain Antibody Pseudomonas, Fusion Protein Directed at Interleukin 2 Receptor Bearing Cells, J. Biol. Chem., vol. 256, No. 25, 1990, pp. 15198–15202.
V.K. Chaudhary, et al., A Rapid Method of Cloning Functional Variable–Region Antibody Genes in *Escherichia coli* as Single–Chain Immunotoxins, Proc. Natl. Acad. Sci. USA, vol. 87, Feb., 1990, pp. 1066–1070.
J.K. Batra, et al., Antitumor Activity in Mice of an Immunotoxin Made with Anti–Transferrin Receptor and a Recombinant Form of Pseudomonas Exotoxin, Proc. Natl. Acad. Sci. USA, vol. 86, Nov., 1989, pp. 8545–8549.
T. Kondo, et al., Activity of Immunotoxins Constructed with Modified Pseudomonas Exotoxin a Lacking the Cell Recognition Domain, J. Biol. Chem., vol. 263, No. 10, 1988, pp. 9470–9475.

*Primary Examiner*—Yvonne Eyler
*Assistant Examiner*—Janet Andres
*Attorney, Agent, or Firm*—Townsend and Townsend and Crew LLP

[57]  ABSTRACT

Single chain immunotoxins directed at the human transferrin receptor using PCR based methods are described. Anti-TFR (Fv)-PE40 contains DNA for the antigen binding portion (Fv) of a monoclonal antibody directed at the human transferrin receptor fused to the DNA for a 40,000 molecular weight fragment of Pseudomonas exotoxin (PE40). In another fusion protein, DT388-anti-TFR(Fv), DNA for the antigen binding portions of the anti-TFR antibody has been fused to the DNA encoding a truncated form of Diphtheria toxin. In anti-TFR(Fv)-PE40, the single chain antibody precedes the toxin whereas in DT388-anti-TFR(Fv) the single chain antibody is at the carboxyl end of toxin. The proteins encoded by these gene fusions were expressed in *E.coli* and purified by conventional chromatographic techniques to near homogeneity.

4 Claims, 4 Drawing Sheets

RECOMBINANT IMMUNOTOXIN COMPOSED OF A SINGLE CHAIN ANTIBODY REACTING WITH THE HUMAN TRANSFERRIN RECEPTOR AND DIPTHERIA TOXIN

BACKGROUND OF THE INVENTION

1. Field of the Invention

The present invention relates to recombinant active single chain immunotoxin fusion proteins which selectively kill cells bearing appropriate antigens or receptors. In particular, the present invention relates to a genetically modified form of diphtheria toxin (DT) and a single chain antibody [anti-TFR(Fv)] that binds to the human transferrin receptor.

2. Background Information

Immunotoxins made by chemically coupling tumor-specific monoclonal antibodies to bacterial or plant toxins including Pseudomonas exotoxin (PE) and Diphtheria (DT) have been shown to possess in vitro and in vivo antitumor activity (Pastan, I. et al., 1986, Cell 47, 641–648; Vitetta, E. S. et al., 1987, Science 238, 1098–1104; Fitzgerald, D. and I. Pastan, 1989, J. Natl. Cancerhzst. 81, 1455–1463). Both PE and DT kill the cells by ADP-ribosylating elongation factor 2 thereby inhibiting protein synthesis. X-ray crystallographic and mutational analysis show the PE molecule is made up of three distinct domains, namely; an amino terminal binding domain, a central translocation domain and a carboxyl activity domain (Allured, V. S. et al., 1986, Proc. Natl. Acad. 2 Sci. USA, 83, 1320–1324; Hwang, J. et al., 1987, Cell, 48, 129–136). Diphtheria toxin however is mainly divided into two chains, A and B, linked by a disulfide bridge. In contrast to PE, chain B of DT which is on the carboxyl end is responsible for receptor binding and chain A which is present on the amino end contains the enzymatic activity (Uchida, T. et al., 1972, Science, 175, 901–903; Uchida, T. et al., 1973, J. Biol. Chem. 248, 3838–3844). Apparently the last 150 amino acids of DT are responsible for its cell binding activity (Uchida, T. et al., 1972, Science, 175, 901–903; Uchida, T. et al., 1973, J. Biol. Chem. 248, 3838–3844; Rolf, J. M. et al., 1990, J. Biol. Chem., 265, 7331–7337).

Immunotoxins have been constructed by attaching antibodies either to native Pseudomonas exotoxin (PE) that has a Mr of 66 kDa or to truncated forms of PE that lack its cell binding domain and have a Mr of about 40 kDa (referred to as PE40). Immunotoxins made with PE40 or LysPE40, a PE40 derivative with an extra lysine residue at its amino terminus that facilitates coupling to antibodies, have a more specific action on target cells because PE cannot bind to its cellular receptor (Pirker, R. et al., 1985, Cancer Res. 45, 751–757; Kondo, T. et al., 1988, J.Biol. Chem., 263, 9470–9475; Batra, J. K. et al., 1989, Proc. Natl. Acad. Sci. USA, 86, 8545–8549). One such immunotoxin, anti-transferrin receptor (TFR)-LysPE40, was shown to be highly cytotoxic to cells expressing the human transferrin receptor and when given intraperitoneally to mice caused regression of A431 tumors growing as subcutaneous xenografts (Batra, J. K. et al., 1989, Proc. Natl. Acad. Sci. USA, 86, 8545–8549). Immunoconjugates with low nonspecific toxicity have also been made by using modified DT with mutations in its cell binding domain which, unlike PE, is present on the carboxyl end of the toxin (Youle, R. J. et al., 1988, In Immunotoxins, Frankel, A. E. (ed.), pp.113–122; Murphy, J. R. F., 1988, In Immunotoxin, Frankel, A. E. (ed), pp.123–140).

Immunotoxins constructed by chemical cross linking are heterogeneous and are difficult to produce in large amounts because the antibody and toxin must be made separately and then conjugated together in a reaction that often has a low yield.

To overcome this problem, a recombinant single-chain immunotoxin has recently been described directed at the P55 subunit of the human (IL-2) interleukin 2 (IL-2) receptor termed anti-Tac(Fv)PE40. It consist of the variable domains of a monoclonal antibody directed at the interleukin-2 receptor arranged in a single chain form linked to the amino terminus of PE40 (Chaudhary, V. K. et al., 1989, Nature, 339, 394–397; Batra, J. K. et al., 1990, J. Biol. Chem. 265, 15198–15202). Recently, Chaudhary et al. constructed anti-Tac (Fv) PE40 from cDNA but such constructs may also be made from RNA. The single chain immunotoxin is constructed starting with hybridoma RNA and using polymerase chain reaction (PCR) to isolate DNA encoding the variable heavy and variable light chains of the antibodies and inserting this DNA into an expression vector containing PE40 sequence (Chaudhary, V. K. et al., 1990, Proc. Natl. Acad. Sci. USA 87, 1066–1070). Anti-Tac(Fv)-PE40 selectively killed cell lines that express the p55 subunit of the human IL-2 receptor. This chimeric protein was also very effective in killing cells activated in a mixed leukocyte reaction (MLR) as well as human phytohemagglutinin-stimulated blasts (Batra, J. K. et al., 1990, J. Biol. Chem., 265, 15198–15202).

Murphy and his coworkers (Williams et al., 1990, J. Biol. Chem 265, 11885–11889) has previously shown that recombinant proteins could be made by fusing the carboxyl end of a mutant form of diphtheria toxin (DT) to the lymphokine, IL-2. In other studies, a fusion protein called DT-388-IL-2 has been prepared that consists of the first 388 amino acids of DT fused to the human IL-2 (V. K. Chaudhary, D. J. Fitzgerald and Ira Pastan, unpublished results). This protein was also very cytotoxic to cells bearing the human as well as the mouse high affinity IL-2 receptor.

Thus, it is clear that a need exists to create recombinant chimeric immunotoxins because of their potential usefulness as antitumor agents. To circumvent the problem of high titer antibodies to PE40 that may arise upon repeated treatment with single chain antibodies linked to PE40, construction of other active single chain immunotoxins are required having different toxin moieties that place the antigen binding portion at either the amino terminus, the carboxyl terminus, or at both termini. The present invention provides the construction of such immunotoxins.

BRIEF DESCRIPTION OF THE DRAWINGS

FIG. 2 shows the SDS-PAGE analysis of (A) anti-TFR (Fv)-PE40 and (B) DT388-anti-TFR(Fv) at different steps of purification. Lane 1, Inclusion bodies; Lane 2, Mono Q pool; Lane 3, TSK gel filtration pool. SDS-PAGE was done using the method of Laemmli (Laemmli, U. K., 1970, Nature, 227, 680–685). The gel was stained with Coomassie blue.

FIG. 4 shows the competition binding analysis of the anti-TFR antibody, HB21, versus anti-TFR(Fv)-PE40. Competition by anti-TFR(Fv)-PE40 (O), HB21-LysPE40 (■), and native HB21 (●) of [$^{125}$I] labeled tracer HB21 on HUT102 (A) and A431 cells (B).

SUMMARY OF THE INVENTION

It is an object of the present invention to provide recombinant active single chain immunotoxins composed of genetically modified forms of toxin that can be attached to single chain antibodies at the toxin's carboxyl end.

In one embodiment, the present invention relates to recombinant active fusion proteins composed of a genetically modified form of diphtheria toxin (DT) called DT-388 that cannot bind to its cellular receptor due to a deletion of amino acids at its carboxyl end and a single chain antibody, wherein the toxin is placed at the amino terminus of either the heavy or light chain variable domain of the single chain antibody.

In another embodiment, the present invention relates to a single chain immunotoxin called DT388-anti TFR(Fv). The single chain protein contains the truncated form of Diphtheria toxin, DT388 fused to the amino terminus of the variable heavy chain domain of transferrin receptor antibody which is connected to its variable light chain through a linker.

In a further embodiment, the present invention relates to a construct comprising DNA fragments encoding the recombinant fusion protein containing a toxin attached through its carboxyl end to a single chain antibody, leaving the toxin's amino terminus remains unaltered.

The invention also relates to a construct comprising DNA fragments encoding the recombinant fusion protein of a truncated Diphtheria toxin in which the binding domain is deleted or altered by another mutation and attached through its carboxyl end to a single chain antibody.

The invention also relates to a construct comprising DNA fragments encoding the recombinant fusion protein of the truncated Diphtheria toxin (DT-388) attached through its carboxyl end to a single chain antibody.

The invention further relates to a construct comprising DNA fragments encoding the above described DT-388 attached through its carboxyl end to the Fv fragment of the transferrin receptor antibody.

In a further embodiment, the present invention relates to recombinant DNA constructs comprising fragments of each of the above described DNA molecules and a vector.

The invention also relates to a host cell stably transformed with such a recombinant construct in a manner allowing expression of DT-388 antibody (Fv) immunotoxin encoded in the DNA fragment.

Another embodiment includes host cells stably transformed with the DT-388-anti-TFR(Fv) construct in a manner allowing the expression of the recombinant DT-388-anti-TFR(Fv) fusion protein.

In yet a further embodiment, the present invention relates to a recombinant immunotoxin such that two different toxin moieties are fused with or without a flexible peptide linker to the antibody, one at the amino and the other at the carboxyl termini of the antibody variable region (Fv).

In another embodiment, the present invention relates to a recombinant immunotoxin where DT-388 is attached at the amino terminus of the antibody variable region and the 40 kda fragment of Pseudomonas exotoxin (PE40) is attached at the carboxyl terminus of the antibody variable region.

In a further embodiment, the present invention relates to a recombinant DNA construct comprising DNA fragments encoding the recombinant fusion protein containing two different toxins attached to a single chain antibody wherein one toxin moiety is fused to the amino end of the antibody variable region and a different toxin moiety is fused to the carboxyl end of the antibody variable region.

Other embodiments of the present invention relate to the recombinant DNA immunotoxin constructs containing two different toxin moieties fused to an antibody variable region at either end and a vector.

In another embodiment, the present invention relates to compositions comprising effective amounts of recombinant immunotoxin fusion proteins that kill cells bearing a receptor or antigen which the antibody variable portion of the recombinant fusion protein binds together with pharmaceutically acceptable carriers.

Various other objects and advantages of the present invention will become obvious from the drawings and the following description of the invention.

All publications mentioned herein are hereby incorporated by reference.

DETAILED DESCRIPTION OF THE INVENTION

The present invention relates, in part, to newly constructed single chain immunotoxins directed at the human transferrin receptor. One of these is anti-TFR(Fv)-PE40 which consists of the variable regions of HB21, a monoclonal antibody to the human transferrin receptor, joined to PE40 a truncated form of Pseudomonas exotoxin devoid of its binding domain. This fusion protein was expressed in *E. coli* and purified to near homogeneity. Anti-TFR(Fv)-PE40 was found to be very cytotoxic to cells bearing human transferrin receptors. The cytotoxicity was specific as shown by competition with excess antibody. To demonstrate that it should be possible to make single chain immunotoxins that have the same antigen binding domain but a different toxin and to compare their activities on different cell types, a second single chain immunotoxin, DT388-anti-TFR(Fv) was constructed containing a truncated form of DT lacking the DT binding activity. This fusion protein also was found to be cytotoxic to the cells expressing the human transferrin receptor.

The present invention further relates to the use of ribosome inactivating agents such as shiga toxin and Ricin A chain with single chain antibody to construct recombinant immunotoxins. Also, cholera toxin may be used which acts by inhibiting the protein synthesis like PE and DT. All the above mentioned toxins like DT are composed of two chains termed A and B. The amino terminal A chain is responsible for the toxin activity and and B chain(s) is responsible for binding to the toxin receptor (Middlebrook J. L. and Dorland R. B., (1984) *Microbiol.Rev*. 48, 199; Olsnes, S. Reisbig, R. and Eiklid, K. (1981) *J. Biol. Chem*. 256, 8732; Mekalanos J. J., Swartz, D. J., Pearson G. D. N., Hartford, N., Groyne, F. and dewilde, M. (1983) *Nature* 306, 551]. Recombinant single chain immunotoxins can be made by placing the Fv on the carboxy end of the truncated toxins lacking the B chains.

The present invention also relates to constructs where the antibody Fv fragment is associated to the toxin directly. However, a peptide linker between Fv fragment and toxin may be helpful in obtaining a better molecule.

The present invention further relates to recombinant fusion proteins produced by an expression vector or plasmid comprising DNA segments which direct the synthesis of the fusion protein.

The present invention also relates to a composition comprises an effective amount of recombinant fusion immunotoxin protein that kill cells bearing a receptor or an antigen to which the antibody binds, and a pharmaceutically acceptable carrier.

The term "antibody" as used herein means a portion of an immunoglobulin molecule (see W. E. Paul, ed., "fundamental Immunology," Raven Press, N.Y., 1984, pp. 131–165) capable of binding to an antigen. According to this definition, the term "antibody" includes various forms of modified or altered antibodies, such as an intact immunoglobulin, an Fv fragment containing only the light and heavy chain variable regions, an Fab or (Fab)'$_2$ fragment containing the variable regions and parts of the constant regions, a single-chain antibody (Bird et al., 1988, *Science* 242, 424–426; Huston et al., 1988, *Proc. Nat. Acad. Sci. USA* 85, 5879–5883), and the like. The antibody may be of animal (especially mouse or rat) or human origin or may be chimeric (Morrison et al., 1984, *Proc. Nat. Acad Sci USA* 81, 6851–6855) or humanized (Jones et al., 1986, *Nature* 321, 522–525, and published UK patent application #8707252). Methods of producing antibodies suitable for use in the present invention are well known to those skilled in the art and can be found described in such publications as Harlow & Lane, Antibodies: A Laboratory Manual, Cold Spring Harbor Laboratory, 1988. The genes encoding the antibody chains may be cloned in cDNA genomic form by any cloning procedure known to those skilled in the art. See for example Maniatis et al., Molecular Cloning: A Laboratory Manual, Cold Spring Harbor Laboratory, 1982.

The invention further relates, in part, to the recombinant DT-antibody fusion protein composed of one polypeptide chain. The production of the single chain fusion protein is illustrated herein. The $V_L$, $V_H$, and DT 388 (a mutant DT with 388 amino acids of DT) genes may occur in any order on the plasmid, that is to say, the DT-388 gene may be attached through its carboxyl end to either the 5' or 3' end of either the light or heavy variable chain gene. Those skilled in the art will realize that additional modifications, deletions, insertions and the like may be made to the antibody and DT-388 or PE40 genes. All such constructions may be made by methods of genetic engineering well known to those skilled in the art (see, generally, Maniatis et al., supra) and may produce proteins that have differing properties of affinity, specificity, stability and toxicity that make them particularly suitable for various clinical or biological applications.

In the example disclosed herein, the $V_L$, $V_H$, and DT-388 or PE-40 genes are contained on a single plasmid. Moreover, after synthesis the recombinant DT-388-antibody protein remains internal to the *E. coli* host cell until purified. However the protein may be secreted into the medium or periplasm by the introduction of a signal sequence at the amino end of the protein.

The invention further relates to expression of the fusion proteins in a variety of host cells, including *E. coli*, other bacterial hosts, yeast, and various higher eucaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eucaryotic cells, the control sequences will include a promoter and preferably an enhancer derived from immunoglobulin genes, SV40, cytomegalovirus, etc., and a polyadenylation sequence, and may include a promoter and preferably an enhancer derived from immunoglobulin genes, SV40, cytomegalovirus, etc., and a polyadenylation sequence, and may include splice donor and acceptor sequences. The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, "Protein Purification", Springer-verlag, N.Y. (1982)). Substantially pure compositions of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or otherwise, such as in developing and performing assay procedures. (See, generally, *Immunological Methods*, Vols. I and II, Lefkovits and Pernis, eds., Academic Press, New York, N.Y. (1979 and 1981)).

The present invention also relates to the recombinant fusion proteins and pharmaceutical compositions particularly useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 9.3% glycine and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate and the like. The concentration of fusion protein in these formulations can vary widely, i.e., from less then about 0.5\5, usually at or at least about 1% to as much as 15 or 20% by weight and will be selected primarily based on fluid volumes, viscosities, body weight and the like in accordance with the particular mode of administration selected.

Thus, a typical pharmaceutical composition for intramuscular injection may comprise 1 ml sterile buffered water, and 10 mg of fusion protein.

A typical composition for intravenous infusion may comprise 250 ml of sterile Ringer's solution,and 10 mg of protein. Actual methods for preparing parenterally administrable compositions will be known or apparent to those skilled in the art and are described in more detail in such publications as Remington's Pharmaceutical Science, 15th ed., Mack Publishing Company, Easton, Pa. (1980), which is incorporated herein by reference.

The present invention further relates to the compositions containing the present fusion proteins or a cocktail thereof (i.e., with other proteins) that can be administered for prophylactic and/or therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

In prophylactic applications, compositions containing the present antibodies or a cocktail thereof are administered to a patient not already in a disease state to prevent the onset of disease. Such an amount is defined to be a "prophylactically effective dose." In this use, the precise amounts again depend upon the patient's state of health and general level of immunity.

Single or multiple administrations of the compositions may be administered depending on the dosage and frequency as required and tolerated by the patient. In any event, the composition should provide a sufficient quantity of the proteins of this invention to effectively treat the patient.

Among various uses of the recombinant fusion proteins of the present invention are included a variety of disease conditions caused by specific human cells that may be eliminated by the toxic action of the protein. One preferred application is the treatment of autoimmune conditions such as graft-versus-host disease, organ transplant rejection, type I diabetes, multiple sclerosis, rheumatoid arthritis, systemic lupus erythematosus, myasthenia gravis and the like caused by T and B cells. The example disclosed herein is illustrative. Another preferred application is for the treatment of cancer, caused by malignant cells of various types. The fusion proteins may also be used in vitro, for example in the elimination of harmful cells from bone marrow before transplant. The antibody portion of the fusion protein is chosen according to the intended use. Proteins on the membranes of T cells that may serve as targets for the antibody include CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte antigens for the antibody are described in Leucocyte Typing III, A. J. McMichael, ed., Oxford University Press, 1987. Antigens found on cancer cells that may serve as targets for the antibody include carcinoembryonic antigen (CEA), the transferrin receptor, P-glycoprotein, c-erbB2, and antigens described in the Abstracts of the Third International Conference on Monoclonal Antibody Immunoconjugates for Cancer (San Diego, Calif. 1988). Those skilled in the art will realize that antibodies may be chosen that bind to antigens expressed on still other types of cells, for example membrane glycoproteins or growth factor or hormone receptors such as epidermal growth factor receptor and the like.

The invention also relates to other chimeric toxins that can be created and be potentially useful as anti-toxin agents. Previous studies by the inventors have shown that anti-TFR-Lys PE40 has a very potent in vivo antitumor activity against A431 epidermoid carcinomas. Thus, other immunotoxin constructs such as anti-TFR(Fv)-PE40 and DT-388-anti-TFR(Fv) may be tested in animals with these tumors to determine the in vivo antitumor activity of single chain immuotoxins.

The invention further relates to active single chain immunotoxins constructions that may be made with different moieties placed either at the amino terminus or the carboxyl terminus of the antigen binding portions of the antibody as required. Thus, one may make active single chain immunotoxins from a wide variety of toxins (plant, bacterial or animal) that are now being made by chemical coupling methods.

While the foregoing invention has been described in some detail for purposes of clarity and understanding, it will be appreciated by one skilled in the art from a reading of this disclosure that various changes in form and detail can be made without departing from the true scope of the invention and appended claims.

The present invention will now be illustrated but is not intended to be limited by the following examples.

EXAMPLES

The following materials were used throughout the examples.

Figure 1A:
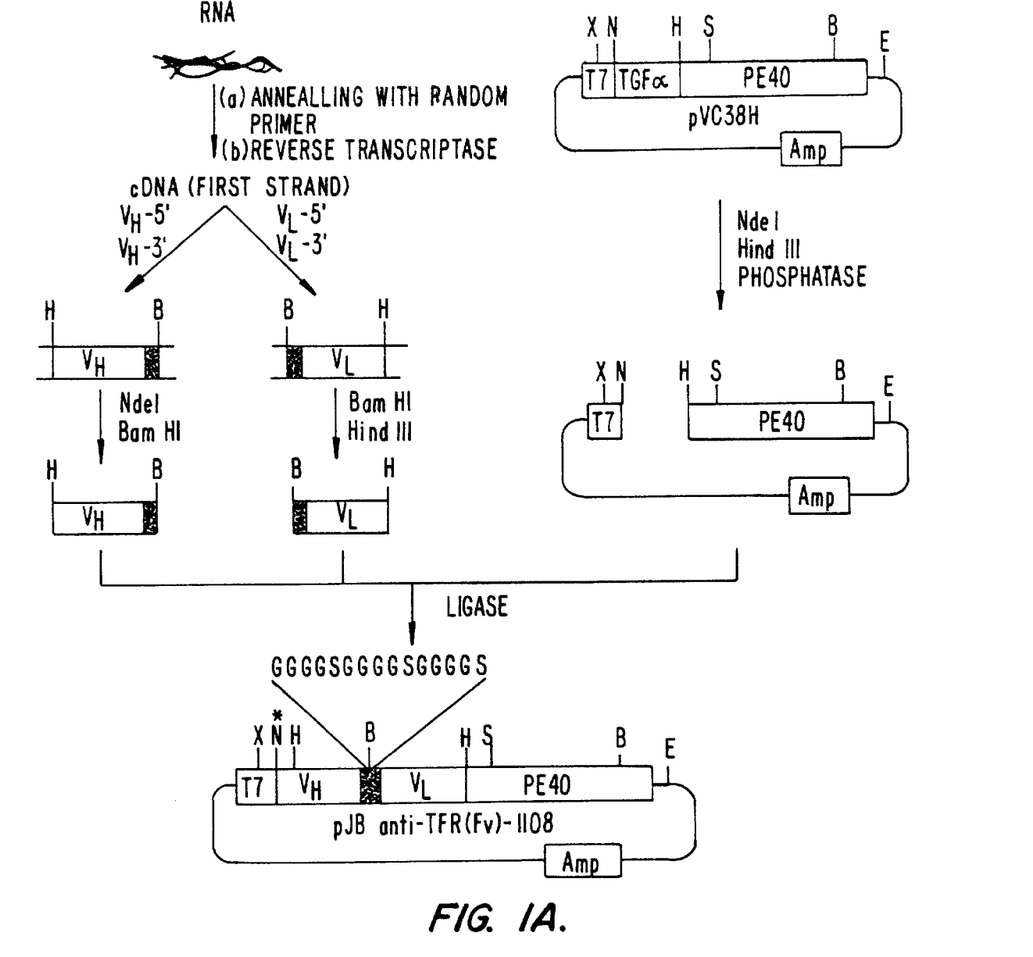
FIG. 1(A) shows the scheme for contruction of plasmid pJB anti-TFR(Fv)-1108 encoding anti-TFR(Fv)-PE40. N, NdeI; B, BamHI; H, HindIII; X, XbaI; S, SalI; E, EcoR1.

Plasmid constructions. The scheme for construction of expression plasmid pJB-anti-TFR(Fv)-1108 encoding anti-TFR(Fv)-PE40 is shown in FIG. 1A. Isolation of RNA, cDNA first strand synthesis and PCR conditions have been described previously in Chaudhary, V. K. et al., 1990, *Proc. Natl. Acad USA*, 87, 1066–1070. The sequences of oligonucleotide primers used to amplify the VH and VL chains by PCR are shown. The purified PCR products were digested with NdeI and BamHI for the fragment encoding VH and part of the linker at its 3' end, or with BamHI and HindIII for VL and rest of the linker at its 5' end. Expression vector pVC38H was digested with NdeI and HindIII and dephosphorylated with calf intestinal phosphatase. The DNA fragments were purified on Sea plaque agarose gel. A three fragment ligation was set up with 3.6 kb dephosphorylated vector, and VH and VL fragments. The recombinants were screened with XbaI and SalI and also with HindIII and BamH1. Several positive clones were checked for protein expression in BL21 ($\lambda$ DE3).

Figure 1B:
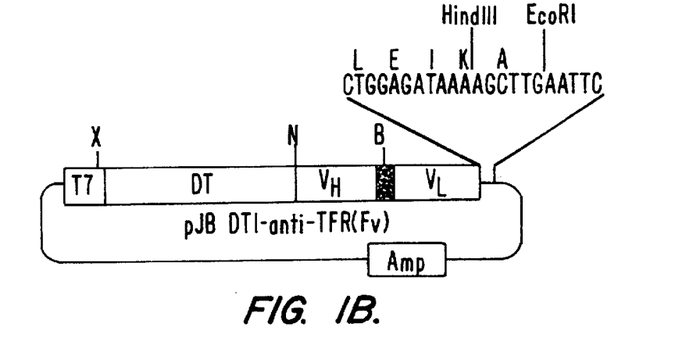
FIG. 1(B) shows the expression of plasmid pJBDT1-anti-TFR(Fv).

FIG. 1B shows the plasmid used for the expression of DT388-anti-TFR(Fv). To construct this plasmid DNA for anti-TFR(Fv) was amplified such that it had a NdeI site at the 5' end and an EcoR1 site at the 3' end by PCR using pJB-anti-TFR(Fv)-1108 as template. The PCR amplified fragment was restricted with NdeI and EcoRl and ligated to pVC DT1-IL2 (Chaudhary, V. K. et al., 1990) digested with NdeI and EcoRI. The recombinants were screened with HindIII and also with BamHI and NdeI. pVC DT1-IL2 contains first 388 codons of DT with initiator methionine fused to CDNA encoding human IL2 (Chaudhary, V. K. et al., 1990). Protein expression and purification BL21 ($\lambda$ DE3) cells were transformed with the plasmids pJB anti-TFR(Fv)-1108 or pJB DTl-anti-TFR(Fv). The cells were grown in superbroth containing 100 $\mu$g ampicillin per ml at 37° C. At OD $_{650}$ of 0.8 cells were induced with 1 mM IPTG. Cells were harvested 90 min later and the location of the fusion protein were determined as described (Chaudhary, V. K. et al., 1987, *Proc. Natl. Acad. Sci. USA* 84, 4538–4542). The fusion protein was isolated from the inclusion bodies by denaturation in 7M guanidine HCl and renaturation by rapid dilution in PBS. The renatured protein was applied after dialysis on 8 ml Q-Sepharose column. Proteins were batch eluted from the column with 0.1, 0.35 and 1 M NaCl. The pool containing the desired fusion protein (0.35 M salt eluate) was diluted and loaded onto a Mono Q 10/10 FPLC column. The fusion protein was eluted by a linear gradient of 0–0.5 M NaCl in 0.02 M Tris pH 7.4. Further purification was achieved by gel filtration chromatography on a TSK 250 column attached to FPLC. The protein concentration was estimated by Bradford's method using BioRad protein assay reagent.

Cytotoxicity assay Cytotoxic activities of anti-TFR(Fv)-PE40, anti-TFR-LysPE40, and DT388-anti-TFR(Fv) were determined by assaying the inhibition of protein synthesis as measured by [³H]-leucine incorporation in a total volume of 1 ml (Chaudhary, V. K. et al., 1989, *Nature*, 339, 394–397). The results are expressed as percent of control where no toxin was added. For competition experiments, 20 μg of antibody was added per well prior to the addition of the toxin (Chaudhary, V. K. et al., 1989, *Nature*, 339, 394–397).

Binding studies [125I] labeled HB21 (20 μCi/μg) as tracer was used at 1.5 ng per assay with varying concentration of competitor with 4×10⁵ HUT 102 cells or 5×10⁵ A431 cells in 0.2 ml binding buffer (RPMI 1640 with 10% FBS,100 μg/ml human immunoglobulin, 0.1% sodium azide) and incubated at room temperature with shaking for 2 hrs. At the end of the incubation cells were washed three times with the binding buffer and counted in a gamma counter (Chaudhary, V. K. et al., 1989, *Nature*, 339, 394–397)

Example 1

Plasmid Construction, Protein Expression and Purification

Figure 2A:
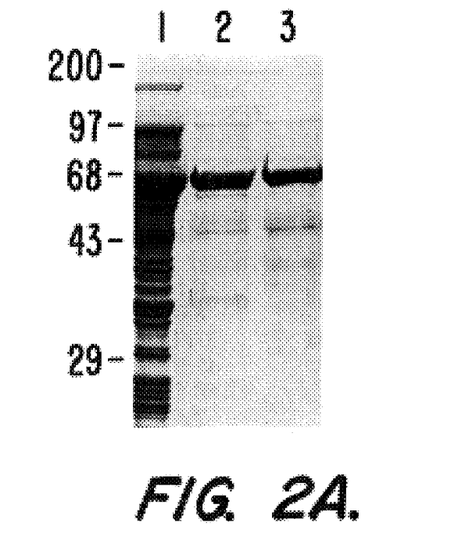
Figure 2B:
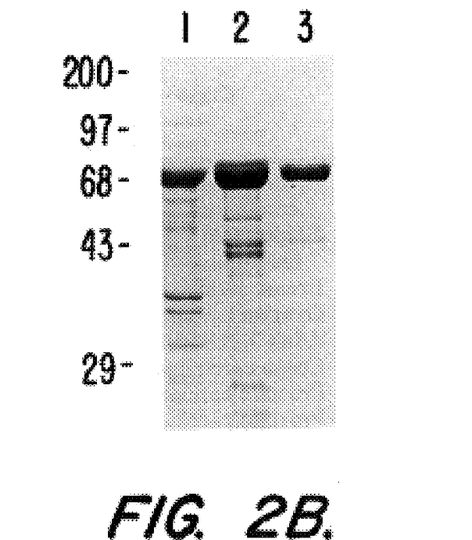

The structure of a plasmid encoding anti-TFR(Fv)-PE40 is shown in FIG. 1A. The assembled gene is under the control of a bacteriophage T7 promoter. The plasmid expresses first ~110 amino acids of anti-TFR heavy chain, a 15 amino acid linker containing (Gly$_4$Ser)$_3$, the first ~100 amino acids of anti-TFR light chain and amino acids 253–613 of PE. The expression plasmid pJB-DT388-anti-TFR(Fv) shown in FIG. 1B encodes the first 388 amino acids of Diphtheria toxin fused to the variable heavy domain of anti-TFR antibody which is connected to its variable light chain through the (Gly$_4$Ser)$_3$ linker. The expression plasmid pJB-DT388-anti TFR(Fv) was deposited on Oct. 30, 1990 at the American Type culture Collection, 12301 Parklawn Drive, Rockville, Md. 20852, USA, and designated at the ATCC as *Esclieiichia coli* HB101, pJB DT1-antiTFR(Fv). The ATCC designation number is 68454. Anti-TFR(Fv)-PE40 and DT388-anti-TFR(Fv) were expressed in *E.coli* (BL21 λ DE3) and after induction with IPTG, the fusion proteins were mostly contained in the inclusion bodies. The fusion protein from the inclusion bodies was denatured in 7M guanidine HCl and renatured by rapidly diluting in PBS. Purification was performed by successive chromatography on a Q-Sepharose anion exchange column followed by a mono Q FPLC column. The pool containing the active protein was finally purified by gel filtration on a TSK 250 FPLC column. The purity of anti-TFR(Fv)-PE40 and DT388-anti-TFR(Fv) at each purification step is shown in FIGS. 2A and B, respectively. The protein after gel filtration chromatography appeared to be >90% pure and used for further studies.

Example 2

Cytotoxicity and Specificity of Anti-TFR(Fv)-PE40.

Figure 3:
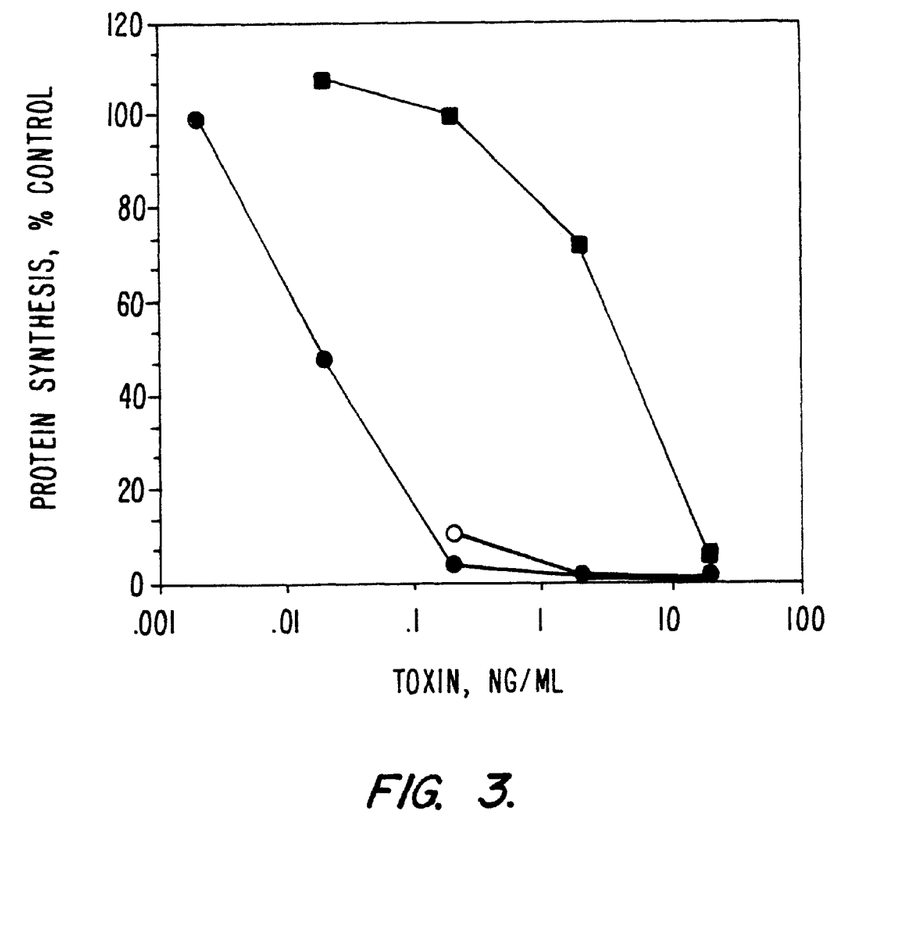
FIG. 3 shows the cytotoxicity of anti-TFR(Fv)-PE40 on A431 cells. Cells were incubated with the toxin for 16–20 hrs, pulsed with $^3H$ leucine and radioactivity was measured in the TCA precipitable protein. Results are shown as percent control where no toxin was added. ●, anti-TFR(Fv)-PE40 alone; O, anti-TFR(Fv)-PE40+20 μg OVB3; a, anti-TFR(Fv)-PE40+20 μg HB21.

As shown in FIG. 3, anti-TFR(Fv)-PE40 was extremely active and inhibited the protein synthesis of A431 cells in a dose dependent manner with an ID$_{50}$, of 0.02 ng/ml or 0.2 pM (Table 1). The cytotoxic effect was blocked by competition with excess anti-TFR, whereas OVB3, a control antibody, did not block the cytotoxicity demonstrating the specificity of anti-TFR(Fv)-PE40 (FIG. 2) for the transferrin receptor. Also, the fusion protein at 2 μg/ml (30 nM) did not inhibit protein synthesis in either mouse Swiss 3T3 or mouse L929 cells reflecting the species specificity of the antibody (Table 1).

TABLE 1

ACTIVITY OF ANTI-TFR(Fv)-PE40 ON VARIOUS HUMAN CELL LINES

| Cells | Origin | ID50 (pM) Anti-TFR(Fv)-PE40 | Anti-TFR-LysPE40⁺ | Relative* Activity |
|---|---|---|---|---|
| A431 | epidermoid Ca | 0.18 | 20 | 111 |
| KB | epidermoid Ca | 0.10 | 75 | 750 |
| MCF 7 | breast Ca | 0.14 | 13.5 | 96 |
| OVCAR3 | ovarian Ca | 8.0 | 1000 | 125 |
| HUT 102 | Adult T-cell leukemia | 37.0 | 50 | 1.3 |
| HT29 | colon Ca | 45.0 | 160 | 3 |
| PC3 | prostate Ca | 58.5 | 280 | 5 |
| LNCAP | prostate Ca | 2.6 | 10 | 4 |
| DU145 | prostate Ca | 92.0 | 400 | 4 |
| L929 | fibroblast (mouse) | >30,000 | >10,000 | — |
| Swiss 3T3 | fibroblast (mouse) | >30,000 | >10,000 | — |

ID$_{50}$ is described as the concentrations of the toxin required to inhibit protein synthesis by 50%.
*Relative activity is the ratio of the activity of Anti-TFR(Fv)-PE40 to the activity of Anti-TFR-LysPE40 on the same cell line.
⁺Anti-TFR-LysPE40 was constructed as described in (Batra, J.K. et al., Proc. Natl. Acad. Sci. USA 86, 8545–8549).

Example 3

Comparison of the Cytotoxic Activity of the Recombinant Immunotoxin with the Chemical Conjugate The activity of anti-TFR(Fv)-PE40 was assayed on a variety of human cell lines and compared with anti-TFR-LysPE40, the chemical conjugate composed of the native antibody and PE40 (Batra, J. K., et al., 1989, *Proc. Natl. Acad. Sci. USA*, 86, 8545–8549). As shown in Table 1, anti-TFR(Fv)-PE40 inhibited protein synthesis in all the human lines studied with ID, Is ranging between 0.10–92 pM. The chemical conjugate anti-TFR-LysPE40 was also toxic to all the cells. However, the ID50's were up to 750-fold lower as compared to the recombinant single chain immunotoxin. Both molecules were inactive on mouse cells demonstrating their specificity for human transferrin receptor (Table 1).

Example 4

Binding of Anti-TFR(Fv)-PE40 to the Transferrin Receptor

Figure 4A:
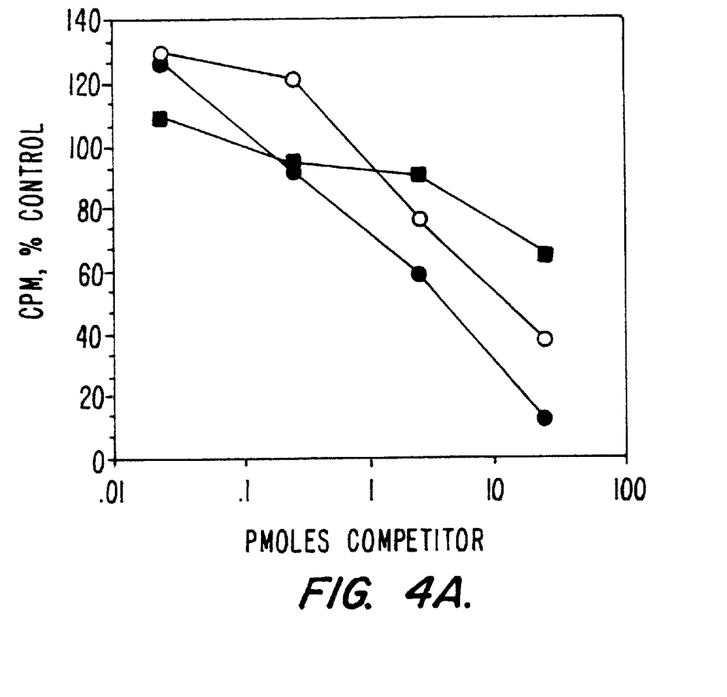
Figure 4B:
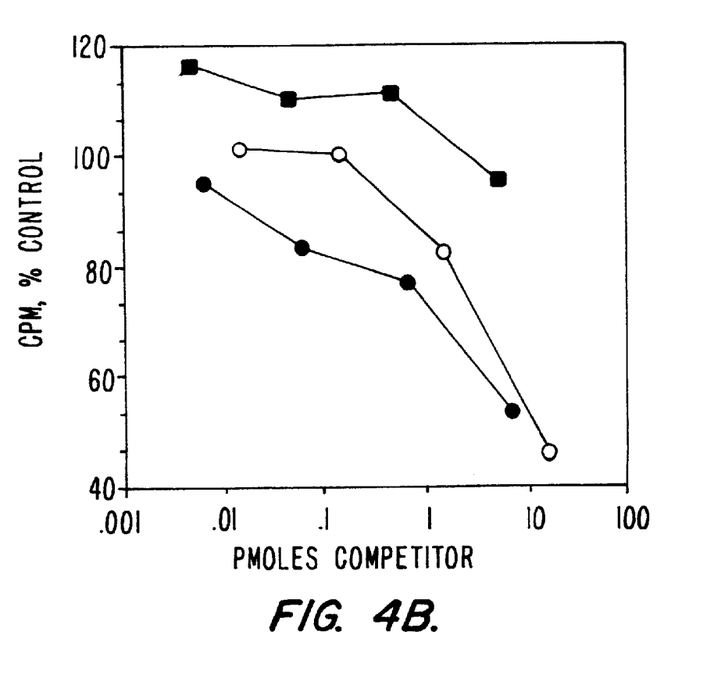

To compare the binding activity of anti-TFR(Fv)-PE40 with the native antibody, competition binding analyses were performed using HUT 102 and A431 cells (FIG. 4). In these studies, the ability of various chimeric toxins to compete for the binding of ¹²⁵I-HB21 (anti-TFR) to A431 cells was determined. Anti-TFR(Fv)-PE40 was shown to compete for binding to the human transferrin receptor very efficiently; its binding affinity was similar to that of HB21 on A431 cells and approximately 2-fold lower on HUT 102 cells. In the same experiments, the chemical conjugate anti-TFR-LysPE40, was tested and found to compete much less well than native HB21. The binding affinity of anti-TFR-LysPE40 appears to be about 10-fold lower than that of then active anti-TFR antibody (FIG. 4).

Example 5

Cytotoxicity and Specificity of DT388-Anti-TFR(Fv)

DT388-anti-TFR(Fv) was also prepared and tested and found to be cytotoxic to several human cell lines with ID$_{50}$2 ranging between 10–100 pM (Table 2). Its cytotoxicity activity was also blocked by excess antibody demonstrating the specificity of DT388-anti-TFR(Fv) for the transferrin receptor. Furthermore, DT388-anti-TFR(Fv) was inactive on mouse L929 cells demonstrating its specificity for human cells (Table 2). When compared with anti-TFR(Fv)-PE40, the DT immunotoxin was 400–800 fold less active on A431, KB and MCF7 cells yet 2–3 fold more active on HUT102 and HT29 cells.

TABLE 2

Activity of DT388-anti-TFR(Fv) on Various Human Cell Lines

| Cells | $ID^{50}$ (pM) | Relative Activity |
| --- | --- | --- |
| A431 | 88 | 500 |
| KB | 82 | 820 |
| MCF7 | 59 | 420 |
| OVCAR3 | 34 | 4 |
| HUT102 | 10 | 0.27 |
| HT29 | 16 | 0.35 |
| L929 | 15,000 | — |

$ID_{50}$ is the concentration of toxin required to inhibit protein synthesis by 50%. Relative activity is the ratio of the activity of anti-TFR(Fv)-PE40 to DT-anti-TFR(Fv) on the same cell line.

What at is claimed is:

1. A DT388-antibody recombinant protein comprising a fusion protein including a diphtheria toxin (DT) portion that consists of the first 388 amino acids of DT, wherein the toxin is at the amino terminus of a heavy chain or light chain variable region of an antibody.

2. The fusion protein of claim 1 wherein the antibody is the antigen binding portion (Fv) of an antibody directed at the human transferrin receptor, said fusion protein called anti-TFR(Fv).

3. The fusion protein of claim 1 wherein the antibody is the antigen binding portion (Fv) of an antibody.

4. A composition comprising an effective amount of the fusion protein as in claim 1, claim 2 or claim 3 to kill cells bearing a receptor or an antigen to which said antibody binds, and a pharmaceutically acceptable carrier.

* * * * *